(12) United States Patent
Bachinski et al.

(10) Patent No.: US 11,478,179 B2
(45) Date of Patent: Oct. 25, 2022

(54) NEURAL DEPTH PROBES AND RELATED SYSTEMS AND METHODS

(71) Applicant: NeuroOne Medical Technologies Corporation, Eden Prairie, MN (US)

(72) Inventors: Thomas Bachinski, Lakeville, MN (US); Mark A. Christianson, Eden Prairie, MN (US); Steve Mertens, Plymouth, MN (US)

(73) Assignee: NeuroOne Medical Technologies Corporation, Eden Pairie, MN (US)

( * ) Notice: Subject to any disclaimer, the term of this patent is extended or adjusted under 35 U.S.C. 154(b) by 475 days.

(21) Appl. No.: 16/593,369

(22) Filed: Oct. 4, 2019

(65) Prior Publication Data

US 2020/0107743 A1 Apr. 9, 2020

Related U.S. Application Data

(60) Provisional application No. 62/741,167, filed on Oct. 4, 2018.

(51) Int. Cl.
*A61B 5/291* (2021.01)
*A61N 1/05* (2006.01)
*H01R 11/09* (2006.01)

(52) U.S. Cl.
CPC ............ *A61B 5/291* (2021.01); *A61N 1/0529* (2013.01); *H01R 11/09* (2013.01)

(58) Field of Classification Search
CPC ...... A61N 1/0529; A61B 5/291; A61B 5/293; A61B 5/294; A61B 5/685; A61B 5/6868; A61B 5/6877; A61B 2562/043; A61B 2562/125; A61B 2562/166
See application file for complete search history.

(56) References Cited

U.S. PATENT DOCUMENTS

| | | | |
|---|---|---|---|
| 5,902,236 A † | 5/1999 | Iversen | |
| 6,024,702 A † | 2/2000 | Iversen | |
| 8,229,539 B1 * | 7/2012 | Motoyoshi | A61B 5/291 607/116 |
| 8,644,903 B1 † | 2/2014 | Osa | |
| 9,498,617 B2 | 11/2016 | Tabada et al. | |
| 2006/0282014 A1 | 12/2006 | Kipke et al. | |
| 2007/0197892 A1 * | 8/2007 | Shen | A61N 1/0529 600/378 |
| 2011/0034977 A1 | 2/2011 | Janik et al. | |
| 2014/0277317 A1 * | 9/2014 | Tooker | A61N 1/0551 607/116 |
| 2014/0324117 A1 | 10/2014 | Bedenbaugh | |
| 2017/0007813 A1 * | 1/2017 | Negi | A61B 5/6868 |

\* cited by examiner
† cited by third party

*Primary Examiner* — Eun Hwa Kim
(74) *Attorney, Agent, or Firm* — Sean Solberg (57) ABSTRACT

Disclosed herein are improved neural depth probes for detection and stimulation, along with various related improved components, devices, methods, and technologies. More specifically, the devices are layered depth electrodes with at least two layers, with each of the layers containing at least one thin-film trace disposed thereon. Each of the devices can also have a plurality of layers with at least two traces on each layer and contacts coupled to each trace.

17 Claims, 7 Drawing Sheets

னேRAL DEPTH PROBES AND RELATED SYSTEMS AND METHODS

CROSS-REFERENCE TO RELATED APPLICATION(S)

This application claims the benefit under 35 U.S.C. § 119(e) to U.S. Provisional Application 62/741,167, filed Oct. 4, 2018 and entitled "Neural Depth Probe and Related Systems and Methods," which is hereby incorporated herein by reference in its entirety.

FIELD

The various embodiments herein relate to neural depth probes, including electrode arrays, and related systems and methods for detection and/or stimulation.

BACKGROUND

Known neural probes and devices have relatively thick profiles that can result in damage to the patient's brain tissue during use. Further, the known devices and technologies are constructed in a scale that is larger than the molecular level, which reduces flexibility and efficiency in construction and modification. In addition, many known devices are too large or are otherwise configured such that they cannot be used in minimally invasive procedures.

There is a need in the art for improved neural depth probes and related devices and technologies.

BRIEF SUMMARY

Discussed herein are various intracranial electrodes, including, for example, depth electrodes having a stacked or layered body made up of at least two layers with thin-film traces disposed thereon.

In Example 1, a intracranial electrode comprises an elongate body comprising a first elongate layer, at least one first layer conductive connector disposed on and along a length of the first elongate layer, a second elongate layer attached to the first elongate layer such that the at least one first layer conductive connector is disposed between the first and second elongate layers, at least one second layer conductive connector disposed on and along a length of the second elongate layer, at least one first layer contact coupled to the elongate body, wherein the at least one first layer contact is electrically coupled with the first side extension, and at least one second layer contact coupled to the elongate body, wherein the at least one second layer contact is electrically coupled with the second side extension. The at least one first layer conductive connector comprises a first side extension extending transversely from a distal end of the at least one first layer conductive connector toward an elongate side of the elongate body, and the at least one second layer conductive connector comprises a second side extension extending transversely from a distal end of the at least one second layer conductive connector toward an elongate side of the elongate body.

Example 2 relates to the intracranial electrode according to Example 1, wherein the at least one first layer conductive connector is a thin-film conductive connector and the at least one second layer conductive connector is a thin-film conductive connector.

Example 3 relates to the intracranial electrode according to Example 1, wherein the at least one first layer contact is disposed around the elongate body and the at least one second layer contact is disposed around the elongate body.

Example 4 relates to the intracranial electrode according to Example 3, wherein the at least one first layer contact is disposed around a full outer circumference of the device body and the at least one second layer contact is disposed around the full outer circumference of the device body.

Example 5 relates to the intracranial electrode according to Example 1, wherein the second elongate layer comprises at least one second layer opening defined in a proximal portion of the second elongate layer, wherein a proximal portion of the at least one second layer conductive connector is disposed through the at least one second layer opening and on and along a length of the first elongate layer.

Example 6 relates to the intracranial electrode according to Example 1, further comprising a third elongate layer attached to the second elongate layer such that the at least one second layer conductive connector is disposed between the second and third elongate layers, at least one third layer conductive connector disposed on and along a length of the third elongate layer, the at least one third layer conductive connector comprising a third side extension extending transversely from a distal end of the at least one third layer conductive connector toward an elongate side of the elongate body, and at least one third layer contact coupled to the elongate body, wherein the at least one third layer contact is electrically coupled with the third side extension.

Example 7 relates to the intracranial electrode according to Example 6, wherein the third elongate layer comprises at least one third layer opening defined in a proximal portion of the third elongate layer, wherein a proximal portion of the at least one third layer conductive connector is disposed through the at least one third layer opening and on and along a length of the second elongate layer.

Example 8 relates to the intracranial electrode according to Example 6, further comprising a fourth elongate layer attached to the third elongate layer such that the at least one third layer conductive connector is disposed between the third and fourth elongate layers, at least one fourth layer conductive connector disposed on and along a length of the fourth elongate layer, the at least one fourth layer conductive connector comprising a fourth side extension extending transversely from a distal end of the at least one fourth layer conductive connector toward an elongate side of the elongate body, and at least one fourth layer contact coupled to the elongate body, wherein the at least one fourth layer contact is electrically coupled with the fourth side extension.

Example 9 relates to the intracranial electrode according to Example 8, wherein the fourth elongate layer comprises at least one fourth layer opening defined in a proximal portion of the fourth elongate layer, wherein a proximal portion of the at least one fourth layer conductive connector is disposed through the at least one fourth layer opening and on and along a length of the third elongate layer.

In Example 10, a depth electrode comprises an elongate body comprising a first elongate non-conductive layer, at least one first layer elongate conductive connector disposed on and along a length of the first elongate non-conductive layer, a second elongate non-conductive layer attached to the first elongate non-conductive layer such that the at least one first layer elongate conductive connector is disposed between the first and second elongate non-conductive layers, at least one second layer elongate conductive connector disposed on and along a length of the second elongate non-conductive layer, at least one first layer contact disposed around the elongate body, wherein the at least one first layer contact is electrically coupled with the first side extension, and at least one second layer contact disposed around the elongate body, wherein the at least one second layer contact is electrically coupled with the second side extension. The at least one first layer elongate conductive connector comprises a first side extension extending transversely from a distal end of the at least one first layer elongate conductive connector toward a side of the first elongate non-conductive layer. The at least one second layer elongate conductive connector comprises a second side extension extending transversely from a distal end of the at least one second layer elongate conductive connector toward a side of the second elongate non-conductive layer.

Example 11 relates to the depth electrode according to Example 10, wherein the at least one first layer elongate conductive connector is a thin-film elongate conductive connector and the at least one second layer elongate conductive connector is a thin-film elongate conductive connector.

Example 12 relates to the depth electrode according to Example 10, wherein the second elongate non-conductive layer comprises at least one second layer opening defined in a proximal portion of the second elongate non-conductive layer, wherein a proximal portion of the at least one second layer elongate conductive connector is disposed through the at least one second layer opening and on and along a length of the first elongate non-conductive layer.

Example 13 relates to the depth electrode according to Example 10, further comprising a third elongate non-conductive layer attached to the second elongate non-conductive layer such that the at least one second layer elongate conductive connector is disposed between the second and third elongate non-conductive layers, at least one third layer elongate conductive connector disposed on and along a length of the third elongate non-conductive layer, the at least one third layer elongate conductive connector comprising a third side extension extending transversely from a distal end of the at least one third layer elongate conductive connector toward a side of the third elongate non-conductive layer, and at least one third layer contact disposed around the elongate body, wherein the at least one third layer contact is electrically coupled with the third side extension.

Example 14 relates to the depth electrode according to Example 13, wherein the third elongate non-conductive layer comprises at least one third layer opening defined in a proximal portion of the third elongate non-conductive layer, wherein a proximal portion of the at least one third layer elongate conductive connector is disposed through the at least one third layer opening and on and along a length of the second elongate non-conductive layer.

Example 15 relates to the depth electrode according to Example 13, further comprising a fourth elongate non-conductive layer attached to the third elongate non-conductive layer such that the at least one third layer elongate conductive connector is disposed between the third and fourth elongate non-conductive layers, at least one fourth layer elongate conductive connector disposed on and along a length of the fourth elongate non-conductive layer, the at least one fourth layer elongate conductive connector comprising a fourth side extension extending transversely from a distal end of the at least one fourth layer elongate conductive connector toward a side of the fourth elongate non-conductive layer, and at least one fourth layer contact disposed around the elongate body, wherein the at least one fourth layer contact is electrically coupled with the fourth side extension.

Example 16 relates to the depth electrode according to Example 15, wherein the fourth elongate non-conductive layer comprises at least one fourth layer opening defined in a proximal portion of the fourth elongate non-conductive layer, wherein a proximal portion of the at least one fourth layer elongate conductive connector is disposed through the at least one fourth layer opening and on and along a length of the third elongate non-conductive layer.

Example 17 relates to the depth electrode according to Example 10, further comprising a third elongate non-conductive layer comprising first and second partial layers and a lumen defined between the first and second elongate non-conductive layers, wherein the lumen extends along a length of the elongate body.

Example 18 relates to the depth electrode according to Example 17, wherein the lumen is constructed and arranged to allow for passage therethrough of a fluid, particulates, a procedural device, a stiffening device, a temperature probe, a steering mechanism, tissue, a treatment composition, or a medication.

In Example 19, a depth electrode comprises an elongate body comprising a stacked configuration of at least two non-conductive thin film layers, a first elongate conductive thin film connector disposed on and along a length of a first layer of the at least two elongate non-conductive thin film layers, the first elongate conductive thin film connector comprising a first side extension extending transversely from a distal end of the first elongate conductive thin film connector toward a side of the elongate body, a second elongate conductive thin film connector disposed on and along a length of a second layer of the at least two elongate non-conductive thin film layers, the second elongate conductive thin film connector comprising a second side extension extending transversely from a distal end of the second elongate conductive thin film connector toward the side of the elongate body, a first contact attached to the elongate body, wherein the first contact is electrically coupled with the first side extension, and a second contact attached to the elongate body, wherein the second contact is electrically coupled with the second side extension, wherein the first elongate conductive thin film connector is disposed between the first and second layers.

Example 20 relates to the depth electrode according to Example 19, wherein the elongate body has a substantially rectangular or substantially square cross-sectional shape.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

BRIEF DESCRIPTION OF THE DRAWINGS

FIG. 10 is an end view of the depth electrode of FIG. 1A, according to one embodiment.

DETAILED DESCRIPTION

The various embodiments disclosed or contemplated herein relate to improved systems, devices, and methods relating to neural depth probes, and various components thereof, for recording neurological signals in the human body. More specifically, the implementations relate to various systems and depth probes for monitoring, stimulating, and/or ablating brain tissue, and various components of such systems and devices. In certain exemplary implementations, the various systems and devices incorporate ultra-thin dielectric materials with thin-film conductive materials placed thereon, thereby resulting in multiple conductors in high density on the devices, which improves the resolution of signal gathering per channel.

In certain implementations, the probes incorporated into the various systems herein can be depth probes (also referred to herein as "depth electrodes" or "electrodes") having thin-film conductors (such as, for example, flexible circuits) incorporated therein. The various depth electrodes disclosed or contemplated herein can not only detect the action potentials of active neurons in the brain, but can also detect the magnitude of the action potentials and the direction from which the action potentials are originating (the "vector" of the action potentials). Thus, in use, as few as three depth electrodes can be used to "triangulate" the location of the brain activity. As such, the use of the depth electrode embodiments as disclosed herein can reduce the number of intrusive electrodes or other devices required to be implanted into the brain in order to locate the target brain activity, thereby reducing trauma to the patient. According to alternative implementations, the various depth electrode embodiments herein can also ablate brain tissue.

For purposes of this application, it is understood that a "thin film" (and "thin-film" as an adjective) is defined as a layer of material of thickness ranging from fractions of a nanometer to tens of micrometers, including up to 100 micrometers. It is understood that thin-film conductors as contemplated herein can be formed by a variety of processes, including spraying, spin-coating, dip-coating, chemical vapor deposition (CVD), evaporation, and sputtering. Thus, the various electrode devices disclosed or contemplated herein are made up of two or more stacked layers, wherein each layer is a thin dielectric layer with at least one thin-film trace discussed deposited thereon.

It is understood that any one of the depth electrode embodiments disclosed or contemplated below and elsewhere herein can incorporate any of the features or components of any of the other depth electrode embodiments herein in any combination.

Figure 1A:
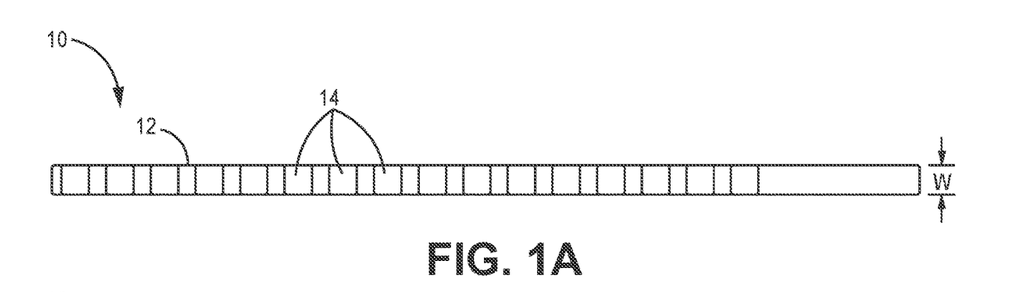
FIG. 1A is a top view of a depth electrode, according to one embodiment.
Figure 1B:
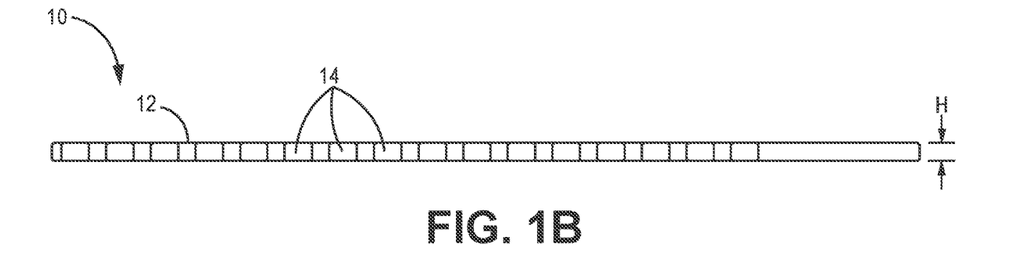
FIG. 1B is a side view of the depth electrode of FIG. 1A, according to one embodiment.
Figure 1C:
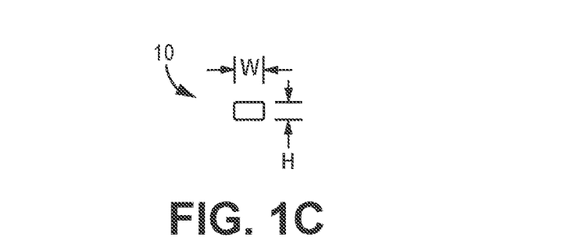

FIGS. 1A-1C depict a depth electrode 10 in accordance with one implementation that is composed of multiple layers as described elsewhere herein that are disposed in a stacked configuration to create a relatively flat probe 10 having a substantially square or rectangular cross-section, according to one embodiment. As best shown in FIGS. 1A-1C, according to certain embodiments, the depth electrode 10 has a body 12 with a width W (as best viewed in the top view of FIG. 1A) that is greater than the height H (as best viewed in the side view of FIG. 1B of the body 12. Thus, the cross-sectional end view of FIG. 10 depicts a substantially flat rectangular body 12. Alternatively, the body 12 can be substantially square such that the cross-sectional shape of the body 12 is substantially square. In one embodiment, both the width W and the height H of the body 12 each range from about 0.5 mm to about 1.5 mm Alternatively, each of the width W and height H can range from about 0.7 mm to about 0.9 mm. Alternatively, both the width W and the height H are about 0.8 mm. Alternatively, the body 12 can have any cross-sectional dimensions. It is understood that, in those embodiments in which the width is greater than the height, the width will fall within one of the ranges as described herein but will be greater than the height, which will also fall within one of the ranges.

The electrode 10 can have a length ranging from about 1 cm to about 10 cm. Alternatively, the electrode 10 and any embodiment herein can have any known length for an electrode. Further, according to one embodiment, the contacts 14 disposed on the body 12 as shown are disposed around the entire outer circumference of the body 12 such that each contact 14 fully encircles the body 12.

Figure 2A:
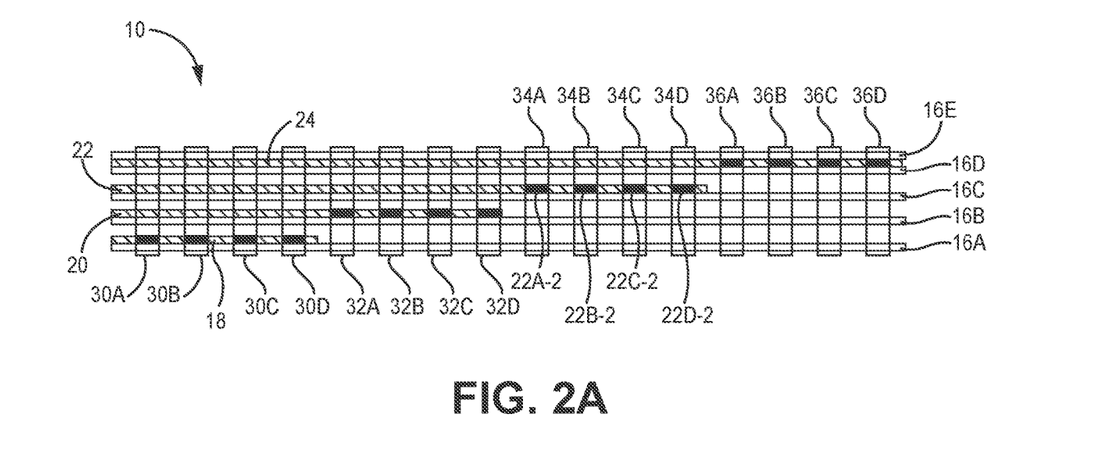
FIG. 2A is a schematic side view of a depth electrode, according to another embodiment.
Figure 2B:
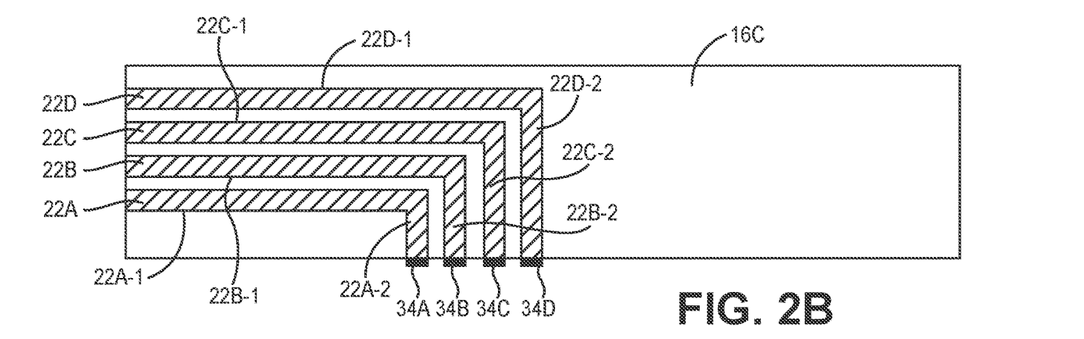
FIG. 2B is a top view of a layer of the depth electrode of FIG. 2A, according to one embodiment.

As mentioned above, the depth electrode 10 has a body 12 that has a layered (or "stacked") configuration. That is, the body 12 is made up of layers of non-conductive thin film with elongate electrical connections (also referred to herein as "traces") disposed therebetween. For example, in one specific embodiment as shown in FIGS. 2A and 2B, the body 12 has four layers of non-conductive thin film 16A, 16B, 16C, 16D and one cover layer 16E with four traces 18, 20, 22, 24 disposed on each of the four layers 16A-16D (as best shown in FIG. 2A). As best shown in FIG. 2B, which depicts a top, cross-sectional view of non-conductive thin film layer 16C with four traces 22A-22D disposed thereon, each of the four traces 22A-22D disposed on the layer 16C is operably coupled to a specific separate one of the contacts 34A-34D and extends from the contact 34A-34D to the proximal end of the probe 10. Each trace 22A-22D is electrically isolated from each other trace 22A-22D disposed on the layer 16C and extends proximally toward a proximal end of the body 12 such that the proximal end of each trace 22A-22D can be coupled to a proximal connector. In one implementation, the proximal connector (not shown) is a known connector such as a ZIF connector or any other known connector for allowing for the electrode 10 and all of the traces 18-24 therein to be electrically coupled to an external controller (not shown) via the proximal connector (not shown). It is understood that each of the other three layers 16A, 16B, 16D has a similar configuration, with four traces on each layer that are similar to the traces 22A-22D on layer 16C except that they differ in the length of their elongate sections (as discussed below) and the four contacts to which they are connected.

Continuing with FIG. 2B, each trace 22A-22D has an elongate section 22A-1, 22B-1, 22C-1, 22D-1 that extends along the length of the layer 16C as discussed above. Further, each trace 22A-22D also has a transverse (or "side") extension 22A-2, 22B-2, 22C-2, 22D-2 that extends from a distal end of the elongate section 22A-1, 22B-1, 22C-1, 22D-1 transversely toward a side of the layer 16C such that each trace 22A-22D is in contact with and electrically coupled to a different, separate contact 34A-34D. More specifically, in this specific example, each of the traces 22A-22D are coupled to a separate one of the four contacts 34A-34D as shown. In one embodiment, each extension 22A-2, 22B-2, 22C-2, 22D-2 is a separate electrical connection that is electrically coupled to the appropriate elongate section 22A-1, 22B-1, 22C-1, 22D-1. Alternatively, each extension 22A-2, 22B-2, 22C-2, 22D-2 is an integral component of the appropriate elongate section 22A-1, 22B-1, 22C-1, 22D-1 such that each trace 22A-22D is a single, unitary component with two sections.

In accordance with one implementation, one advantage of a layered configuration of an electrode in which the traces 18-24 are disposed on layers 16A-16D of non-conductive thin film is that no through-holes or openings need to be formed in the body 12. Instead, the layered configuration of the body 12 and the positioning of the transverse extensions (such as extensions 22A-2, 22B-2, 22C-2, 22D-2 as discussed above and depicted in FIG. 2B) of each trace 18-24 (such as traces 22A-22D) on the non-conductive layers 16A-16D result in the extensions (such as extensions 22A-2, 22B-2, 22C-2, 22D-2) extending beyond the side of the each layer 16A-16D. As such, the extensions (such as extensions 22A-2, 22B-2, 22C-2, 22D-2) are positioned to contact the appropriate contacts (such as contacts 34A-34D as shown in FIG. 2B), thereby resulting in electrical connection between the traces 18-24 and the contacts 30A-36D without the need to form any openings or through-holes in the body 12.

Returning to FIG. 2A, according to one embodiment, the stacked configuration of the body 12 provides for four different traces (like traces 22A-22D in FIG. 2B as discussed above) per layer 16A-16D, such that each layer 16A-16D provides for contact to four separate contacts 18-24. Thus, as shown in FIG. 2A, the four traces 18 disposed on the first (bottom) layer 16A are electrically coupled to the four contacts 30A-30D disposed near the proximal end of the body 12. Further, the four traces 20 disposed on the second layer 16B are electrically coupled to the four contacts 32A-32D disposed just distal to the four proximal-most contacts 30A-30D. In addition, the four traces 22A-22D disposed on the third layer 16C are electrically coupled to the four contacts 34A-34D disposed just proximal to the four distal-most contacts 36A-36D. Finally, the four traces 24 disposed on the fourth layer 16D are electrically coupled to the four contacts 36A-36D disposed near the distal end of the body 12. Thus, in this specific electrode 10 embodiment, with four separate traces on each of four different layers, there are a total of 16 traces 18-24, with each one connected to a different one of 16 different contacts, as best shown in FIG. 2A. It is understood that FIGS. 2A and 2B are simply schematic representations of the stacked configuration and the positional and structural relationships between the layers 16A-16E, the traces 18-24, and the contacts 30A-36D, and that any body 12 could have fewer or more layers and fewer or more traces per layer, and thus any such alternative embodiment could have any desired number of traces and contacts.

In certain configurations, the traces (such as traces 18-24 of the device 10 discussed above) on certain layers are disposed through openings (or "through-holes") at or near the proximal end of the body (such as body 12) so that the proximal end of each trace can extend through the openings to a common layer, thereby resulting in all the traces extending all the other layers such that they are all disposed on the same layer, thereby facilitating connection of each trace to the proximal connector (not shown). The through-holes (not shown) are disposed transversely to the plane of each layer such that the through-holes extend across multiple layers. As a result, at or near the proximal end of the body, each of those traces extends through a through-hole from its original layer to a single layer to which all traces extend. According to one embodiment, the common layer to which the proximal end of all traces extends is the lowest layer (or base layer) of the body. The proximal connector (not shown) is disposed at, near, or adjacent to the lowest layer such that the proximal end of each trace extends into the connector (not shown).

Figure 4A:
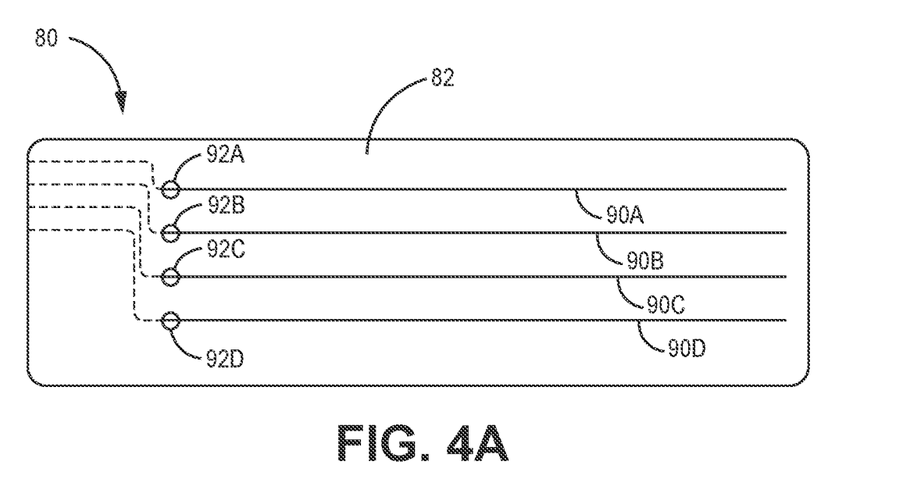
FIG. 4A is a top view of a portion of a layer of a depth electrode, according to one embodiment.
Figure 4B:
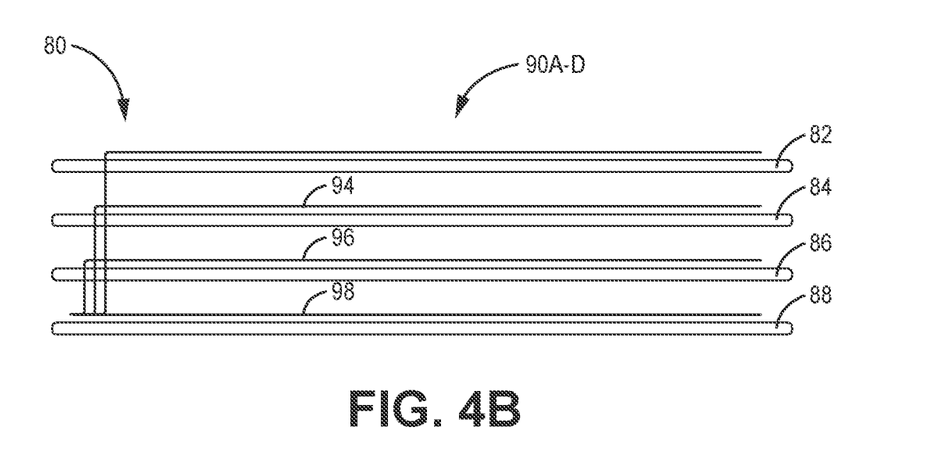
FIG. 4B is a schematic side view of the portion of the layer of the depth electrode of FIG. 4A, according to one embodiment.

One example of such a configuration of through-holes in a layered device 80 according to one embodiment is depicted in FIGS. 4A and 4B. FIG. 4A depicts a top view of the top layer 82 of the device 80 according to one embodiment. Four traces 90A, 90B, 90C, 90D are disposed such that they extend along the length of the layer 82. At the proximal end of the layer 82 as shown, each of the traces 90A, 90B, 90C, 90D is disposed through a separate one of the four openings 92A, 92B, 92C, 92D formed in the layer 82. As best shown in FIG. 4B, which is a side view of the layered device 80 showing the four layers 82-88, the traces 90A-90D extend transversely through the openings 92A-92D in layer 82 and through corresponding openings in layers 84 and 86 such that the traces 90A-90D extend to the bottom layer 88 and are positioned such that they extend along the surface of the bottom layer 88 as best shown in FIG. 4A. Similarly, the traces 94 (of which only one trace 94 is visible because of the perspective) on the second layer 84 extend through openings (not shown) in layer 84 and layer 86 such that the traces 90 extend to and are disposed on the bottom layer 88 in a fashion similar to the traces 90A-90D such that each trace is electrically isolated from all other traces. Further, the traces 96 (of which only one trace 96 is visible) on the third layer 86 extend through openings (not shown) in layer 86 such that the traces 96 extend to and are disposed on the bottom layer 88 in a fashion similar to the traces 90A-90D. Finally, the traces 98 (of which only one trace 98 is visible) on the bottom layer 88 are disposed on the layer 88 and extend to the proximal end of that layer 88. It is understood that each of layers 84, 86, 88 can also have four traces 94, 96, 98 in a fashion similar to layer 82. Alternatively, any number of traces (with any corresponding number of openings or through-holes) can be disposed on the layers, and any number of layers can be provided. In this configuration, all the traces 90A-90D, 94, 96, 98 are disposed at their distal ends on the appropriate layer 82, 84, 86, 88 and all extend proximally, and the traces 90A-90D, 94, 96 disposed on the layers 82, 84, 86 above the bottom layer 88 extend through separate openings toward the bottom layer 88 until all of the traces 90A-90D, 94, 96, 98 are disposed at the proximal end of the layer 88 and all are electrically isolated from each other.

Thus, according to one embodiment in which each layer 82, 84, 86, 88 has four traces, four holes 92A-92D are formed through the top layer 82 to separately receive traces 90A-90D, eight holes are formed through the second layer 84 to separately receive traces 90A-90D, 94, and twelve holes are formed through the third layer 86 to separately receive traces 90A-90D, 94, 96. In one implementation, the through-holes are formed via laser. Alternatively, the openings are formed via any known method or process.

In accordance with one embodiment, the thin non-conductive layers of any of the device embodiments disclosed or contemplated herein can be made of polyimide, mylar, or a dielectric non-conductive film. Alternatively, the non-conductive thin layers can be made of any non-conductive material that can be used in thin-film technology. In one embodiment, the non-conductive layer in to any device implementation herein has a thickness ranging from about 2000 Angstroms to about 0.005 inches. Alternatively, the thickness can range from about 0.001 inches to about 0.0005 inches. In a further alternative, the layer can have a thickness ranging from about 0.005 inches to about 0.001 inches. Alternatively, the non-conductive layer can have a thickness ranging from about . . . . In a further alternative, the non-conductive layer is at least about 2000 Angstroms in thickness.

According to one implementation, the traces of any embodiments disclosed or contemplated herein are thin-film conductive electrical components, each of which is positioned on a layer via a photolithography or photoengraving process, as will be described in further detail below. Alternatively, the traces according to any implementation can be positioned on the layers via any known method or process. It is further understood that any known term for "trace" can be used herein as well.

The contacts, according to any embodiments disclosed are contemplated herein, are made of thin conductive film. For example, the contacts can be made of copper, nickel, gold, titanium, or platinum. Alternatively, the contacts in any implementation can be made of any conductive material.

In one implementation, the contacts are disposed around the outer circumference of the body via a deposition process. More specifically, in one embodiment, the contacts are deposited via a known deposition process called edge plating, as will be described in further detail below. Alternatively, each of the contacts can be positioned or disposed around the entire circumference of the body via any known method or process.

It is understood that the various contacts (and thus the devices) in any of the various implementations herein can be used for sensing (or recording), for stimulation, for ablation, or for any other known purpose in a neural electrode.

According to certain alternative embodiments, the various depth electrode embodiments disclosed or contemplated herein can have sensors incorporated therein. For example, in certain implementations, one or more temperature sensors can be incorporated into any depth electrode device as disclosed herein. Alternatively, any other known sensors that can be used with depth electrodes can be used.

In one specific implementation as discussed above, the depth electrode 10 described above has four layers 16A, 16B, 16C, 16D. Further, it is understood that any embodiment disclosed or contemplated herein can be modified to have one layer, two layers, three layers, five layers, six layers or any number of layers, along with the appropriate number of additional components (such as traces, contacts, etc.) and other features to ensure the operability of the device. Similarly, while the specific exemplary electrode 10 above has 4 traces per layer, it is understood that any number of traces can be disposed on each layer as desired/necessary for the electrode.

In accordance with one embodiment, the benefit of the stacked configurations according to the various embodiments herein is that the layers impart unique structural and/or mechanical features on these implementations in comparison to depth electrodes that do not have a stacked configuration. That is, the stacked configuration provides additional stiffness, directionality, softness, and flexibility. More specifically, the use of layers of different thicknesses in combination with different adhesives makes it possible to modify the mechanical properties of the device embodiments herein, including flexibility, rigidity, bending memory, torque, and other such characteristics. Additionally, portions of one or more of the layers or materials therein may be supplemented with additional material or removed (via laser cutting or any known process) to provide specific material changes that result in predetermined changes to the mechanical properties of the device.

According to one embodiment, any stacked device implementation as disclosed or contemplated herein with contacts disposed around the entire circumference of the device body can be made in the following fashion. First, in one embodiment in which the device has four non-conductive layers (such as layers 16A, 16B, 16C, 16D discussed above), the separate non-conductive layer panels (also referred to as "sheets") are first coated, layered, or cladded with a conductive material. For example, in one embodiment, the sheets are coated with copper. More specifically, in one exemplary embodiment, the copper layer is 0.5 oz copper. The conductive layer on each separate layer panel is then coated with a photoresist material. Once each non-conductive sheet has both the conductive and photoresist layers, each such photoresist layer is exposed to an image of the desired electrically conductive pattern. After exposure, the unexposed photoresist material and underlying conductive layer are removed, thereby leaving each non-conductive layer sheet with four conductive traces (similar to the traces 16A, 16B, 16C, 16D depicted and discussed above) disposed thereon in the desired layout.

According to one embodiment, the separate non-conductive layer panels are templates that are longer and wider than the resulting non-conductive layers after the separate sheets have been processed and formed into the device body as described herein. For example, FIG. 3A depicts a sheet template 40 from which a non-conductive layer (such as layer 16C as described above, for example) is formed, as will be described in additional detail below.

Once the conductive traces have been positioned or formed on the four non-conductive layer sheets, the four separate sheets are stacked or otherwise positioned on each other such that the resulting structure is a layered configuration of four non-conductive layers with four conductive traces disposed on each such layer. According to one embodiment, the four separate layers (or other number of layers in other embodiments) are aligned via index holes (not shown) defined in the sheets that can be used in combination with positioning rods (not shown) to ensure that the four layers are aligned in relation to each other as desired. When the four sheets are placed in aligned contact with each other, an adhesive is used between each layer to ensure that the sheets are adhered to each other to form the stacked set of sheets.

Figure 3A:
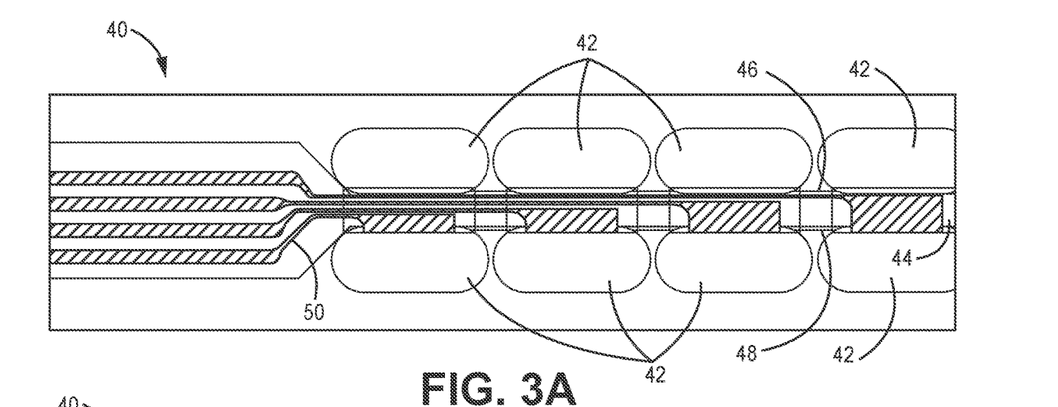
FIG. 3A is a top view of a sheet template for a non-conductive layer of a depth electrode, according to one embodiment.

Once the stacked set of sheets is formed, as best shown in FIG. 3A, the transverse through-holes as described above (such as through-holes 92A-92D, for example) are formed at a proximal portion of the sheet stack. Alternatively, the through-holes are formed before the sheets are stacked onto each other. Once the openings are formed according to a configuration identical or substantially similar to the configuration described above with respect to FIGS. 4A and 4B, according to one embodiment, each opening is coated with a conductive adhesive and then plated with a conductive material. In one embodiment, the conductive material is copper. Once the adhesive and conductive material is added, the traces are positioned through the openings and extended from their original layer to the common layer with which all the openings are in communication.

Figure 3B:
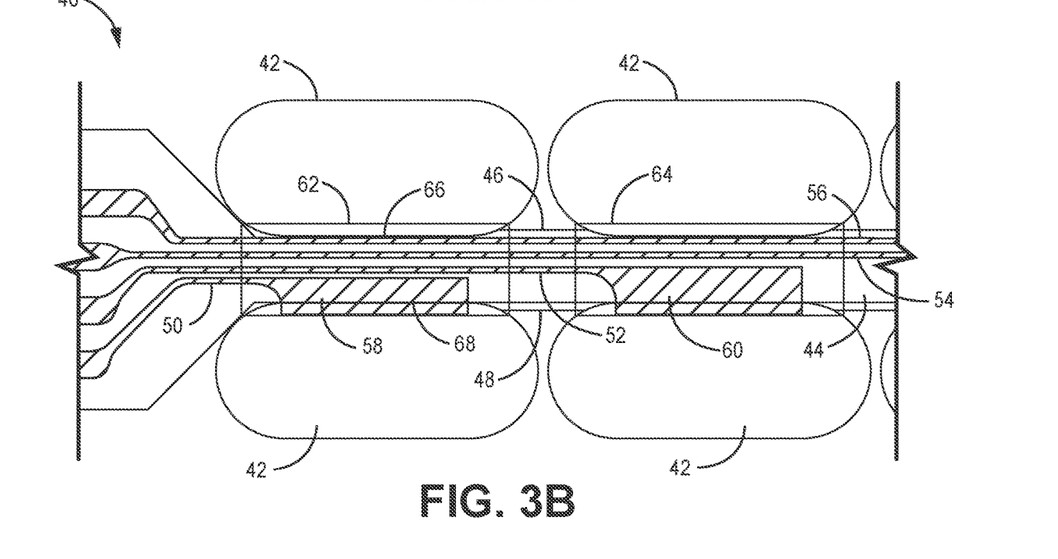
FIG. 3B is an expanded view of a portion of the sheet template of FIG. 3A, according to one embodiment.

In addition, as best shown in FIGS. 3A and 3B, after the sheets have been stacked such that the stacked template 40 is formed, the device can then be formed out of the template. For purposes of this discussion, the device body 44 and the sides 46, 48 thereof that will ultimately be formed out of the template 40 are depicted in schematic fashion in FIGS. 3A and 3B to show how the final product is produced from the template 40. Further, as best shown in FIG. 3B, the four traces 50, 52, 54, 56 disposed on the top sheet of the template 40 are shown as well. In addition, FIG. 3B also shows the side extensions 58, 60 of traces 50, 52, respectively, extending out toward the side 48. Finally, the contacts 62, 64 that will be disposed over the body 44 and in contact with extensions 58, 60, respectively, are depicted schematically as well.

The contacts 62, 64 are formed in the following fashion. First, transverse openings 42 are formed through the stack of sheets along each side 46, 48 of the body 44. That is, openings 42 are formed across all of the layers of the stack 40 in a direction that is transverse to the plane of the sheets 40. As such, the inner wall of each opening 42 is formed into the side 46, 48 so as to carve out a notch or groove 66, 68 in each side 46, 48 as shown. In addition to forming the notches 66, 68 into which the contact 62 can be deposited as described in further detail below, the notch 68 exposes the trace extensions (such as extension 58 as best shown in FIG. 3B) such that the exemplary trace extension 58 (and all other trace extensions in the device) is in fluid communication with the notch 68 and thus can be in electrical contact with the contact 62 that will deposited thereon. Once the representative notches 66, 68 (and all other corresponding notches on the template stack 40) are formed, a conductive adhesive is coated over the notches 66, 68 (and all other notches) and around the entire circumference of the layers. Subsequently, the conductive material is deposited over the adhesive around the entire circumference of the body 44, thereby creating the representative circumferential contact 62 (and all other contacts). According to one embodiment, the conductive material is deposited via a deposition process called edge plating such that the process is applied around the entire circumference of the body 44. The edge plating process, in accordance with one implementation, allows for an automated application of the contacts, rather than manual or hand assembly. Alternatively, any deposition process or any other known method or process for placing a contact around the entire circumference of the body 44 can be used.

In certain embodiments, the conductive material deposited over the adhesive to create the contact 62 (and all other contacts on the device) is copper. According to certain implementations, nickel is then deposited on the copper, and then platinum is deposited on the nickel to complete the contact 62. Alternatively, any known conductive materials can be placed in the representative notches 66, 68 in the corresponding sides 46, 48 and over the corresponding top and bottom portions of the body 44 to create the representative contact 62 (and all other contacts).

Once all of the contacts (including contact 62) have been disposed circumferentially around the body 44 (in their respective notches like notches 66, 68 as discussed above), the body 44 is still attached to the template 40 and thus can be tested for various known characteristics (such as, for example, resistance, continuity, dimensions, etc.) prior to being removed from the template 40. Once any testing is completed, the body 44 can be removed from the template 40. In one implementation, the body 44 is removed using a laser to cut the body 44 from the template 40. Alternatively, any method or process can be used to remove the body 44 from the template 40.

In accordance with certain implementations, the process of manufacturing any of the depth electrode embodiments disclosed or contemplated herein can be an automated process with little human interaction. Thus, in certain implementations, the steps described above for making the electrode can be performed via automation, thereby resulting in increased accuracy and precision for the process in comparison to a non-automated or manual process.

According to other embodiments, the process disclosed herein is also scalable. In one embodiment, the scalability results from the fact that the process can be automated.

Figure 5:
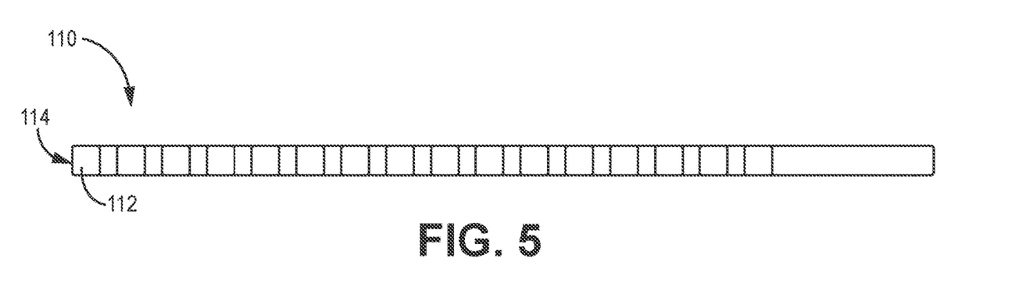
FIG. 5 is a side view of another depth electrode, according to another embodiment.

FIG. 5 depicts another embodiment of a device 110 which is configured and constructed in a fashion similar to the implementations described above. In this specific embodiment, the distal-most contact 112 is disposed at the distal end of the device 110 such that the conductive material of the contact 112 is also disposed on the distal tip 114 of the device. The contact 112 and the trace (not shown) coupled thereto are constructed and configured in a fashion similar to the other device embodiments disclosed or contemplated herein.

Figure 6:
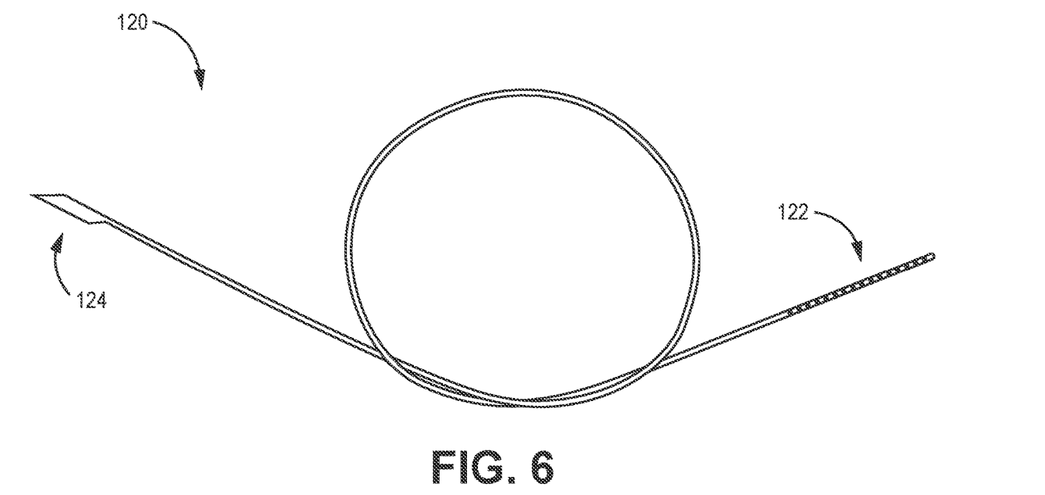
FIG. 6 is a perspective view of a further depth electrode, according to a further embodiment.

FIG. 6 depicts one embodiment of a device 120 as contemplated herein, with contacts at the distal end 122 and the connector 124 at the proximal end.

Figure 7:
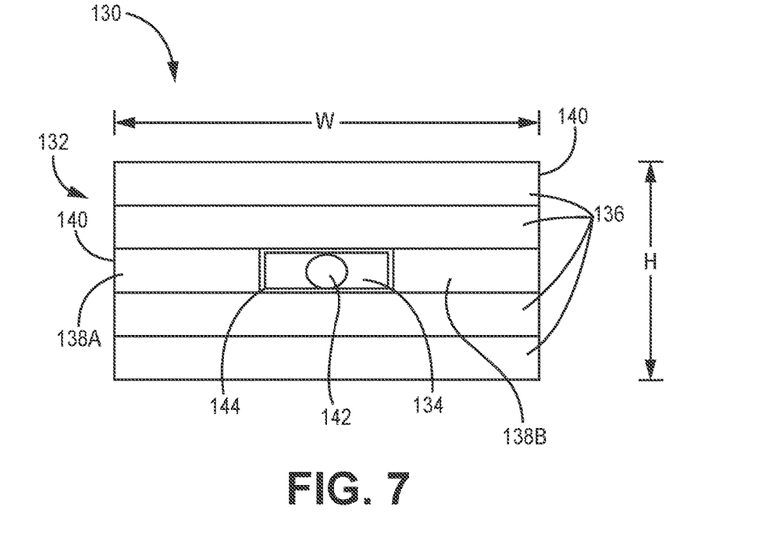
FIG. 7 is an end view of yet another depth electrode, according to another embodiment.

In accordance with an alternative embodiment as best shown in FIG. 7, a layered depth electrode 130 is provided herein with a lumen 134 defined within the body 132 and disposed along the length of the body 132 such that the lumen 134 in one embodiment extends from a first end (not shown) of the body 132 to a second end (not shown) thereof. It is understood that the device 130 embodiment can have substantially the same components, features, and configurations as the other layered device embodiments discussed or contemplated herein and can be constructed and used in a similar fashion to those embodiments as well. As such, the corresponding components and features in this device 130 will not be discussed in detail except as to the components and features that differ in this embodiment.

As with the other implementations herein, the depth electrode 130 is composed of multiple thin film layers 136 (five layers 136 in this specific instance) that are disposed in a stacked configuration that forms the body 132 with a width W that is, in certain embodiments, greater than the height H. In addition to the same stacked layers as the embodiments elsewhere herein, the instant implementation as shown has two elongate partial layers (also referred to as "partial sheets" or "lateral fillers") 138A, 138B. As can be seen in FIG. 7, each of the lateral fillers 138A, 138B is disposed along a side or outer edge 140 of the body 132 and has a width that is less than half of the width of the layers 136. As such, the resulting gap that is formed between the two fillers 138A, 138B is the lumen 134 as shown.

According to certain embodiments, the lumen 134 can be used to receive a device stiffener, a temperature probe, a biopsy device, a steering mechanism, or any other known device that could be used in conjunction with a depth electrode such that the device can be disposed within or inserted into the lumen 134. In a further alternative, the lumen 134 can be used for drug delivery or any other known purpose. In certain specific embodiments such as the specific depiction in FIG. 7, a cannula 142 or any other known type of tube can be disposed through the lumen 134 and the various devices described above can be inserted through the cannula 142 and/or the various procedures contemplated herein can be performed through the cannula 142. In certain implementations, the cannula 142 is disposed through the lumen 134 and the remaining space in the lumen 134 surrounding the cannula 142 remains open space. Alternatively, the remaining space in the lumen 134 surrounding the cannula 142 can be filled in with any known material or filler of any kind such that the only open space is the space defined by the cannula 142.

According to certain embodiments, including the embodiment depicted in FIG. 7, a liner (also referred to as a "lining," "inner sheath," "inner wall," or "inner layer") 144 is disposed within the lumen 134 and positioned such that the walls of the liner 144 are disposed along or adjacent to the inner walls of the lumen 134. The exemplary liner 144 as shown has a substantially rectangular or square shape, but it is understood that the liner 144 can also be substantially circular or ovular. Alternatively, the liner 144 can have any known shape. In one implementation, the liner 144 prevents any adhesive applied or otherwise disposed between the layers 136 to seep into or otherwise encroach into the lumen 134. As such, the liner 144 can help to prevent the lumen 134 from being filled or somewhat obstructed with adhesive or other materials. Of course, it is understood that certain embodiments don't have a liner.

Further alternative embodiments of layered depth electrodes include depth electrodes having contacts that don't fully encircle the entire circumference of the device body, but instead are each disposed on a single side of the four-sided electrode body. Such depth electrode embodiments include those depicted in FIGS. 8A-10C, as will be discussed in further detail below.

Figure 8A:
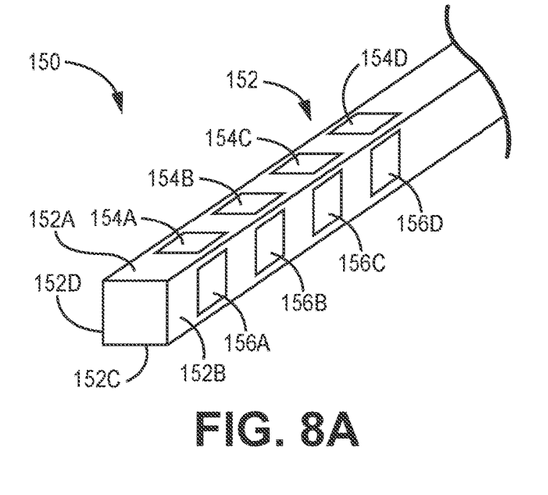
FIG. 8A is a perspective view of a distal portion of another depth electrode, according to another embodiment.
Figure 8B:
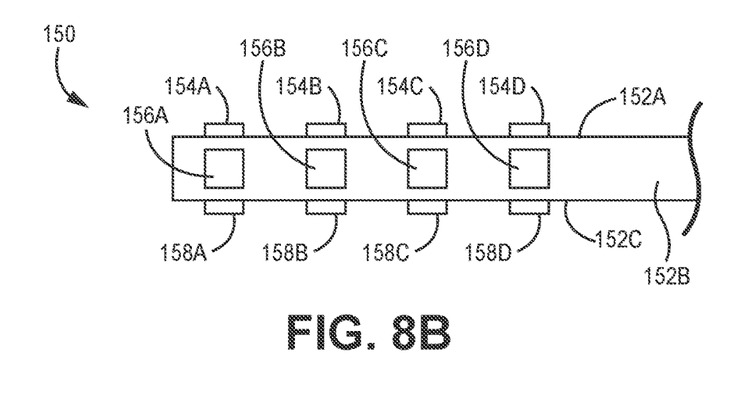
FIG. 8B is a side view of the distal portion of the depth electrode of FIG. 8A, according to one embodiment.
Figure 8C:
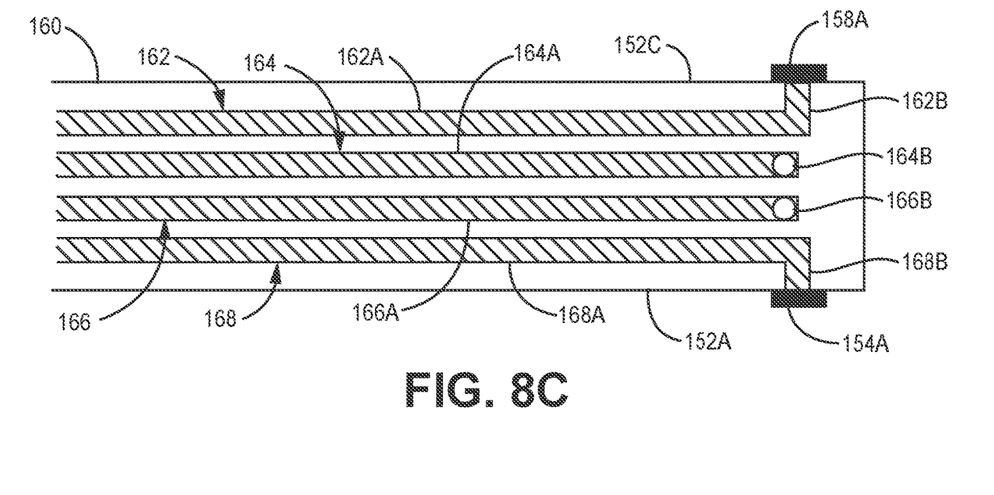
FIG. 8C is a top view of a distal portion of a layer of the depth electrode of FIG. 8A, according to one embodiment.

FIGS. 8A-8C depict a layered depth electrode 150 in accordance with one implementation that is composed of multiple thin film layers that are disposed in a stacked configuration to create a probe 150 having a relatively square or flat cross-section, according to one embodiment. As best shown in FIGS. 8A and 8B, the depth electrode 150 has a substantially square body 152. Alternatively, the body 152 can be substantially rectangular. It is understood that this body 152 and any other device body 152 disclosed or contemplated herein can have dimensions similar to those described above with respect to body 12. Alternatively, the body 152 can have any cross-sectional dimensions and length.

Further, according to one embodiment, the body 152 has contacts 154A-158D, each of which is disposed on a side of the body 152. The contacts 154A-158D in this specific implementation are substantially square, but it is understood that the contacts 154A-158D can have any shape, including circular, quadrilateral, or any other known shape. Thus, the body 152 has a first side 152A with four contacts 154A, 154B, 154C, 154D disposed thereon, a second side 152B with four contacts 156A, 156B, 156C, 156D disposed thereon, a third side 152C with four contacts 158A, 158B, 158C, 158D disposed thereon (as best shown in FIG. 8B), and a fourth side 152D (as best shown in FIG. 8A) with four contacts (not shown due to the perspective of the figures) disposed thereon. More specifically, there are four sets of four contacts that are disposed at the same position along the length of the body 152 but on a different side 152A-152D thereof. Thus, the first set of four contacts 154A, 156A, 158A, 160A (not shown) is disposed near the distal end of the body 152, while the second set of four contacts 154B, 156B, 158B, 160B (not shown) is disposed adjacent to the first set. Further, the third set of four contacts 154C, 156C, 158C, 160C (not shown) is disposed adjacent to the second set. and the fourth set of four contacts 154D, 156D, 158D, 160D (not shown) is disposed adjacent to the third set (and most distant from the distal end). Unlike other embodiments herein, none of the contacts on this electrode 150 encircle the body 152, and instead are disposed solely on one side of the body 152 as shown.

As mentioned above, the depth electrode 150 has a body 152 that has a layered (or "stacked") configuration in a fashion similar to the other device embodiments herein. That is, the body 152 is made up of layers of non-conductive thin film with traces disposed therebetween. For example, in one specific embodiment, the body 152 has four layers of non-conductive thin film (not shown) in a fashion similar to the device 10 depicted in FIG. 2A with four traces (not shown) disposed on each of the four layers (not shown). For example, as best shown in FIG. 8C, which depicts a top, cross-sectional view of one exemplary non-conductive thin film layer 160 (of the four layers of the body 152) with four traces 162, 164, 166, 168 disposed thereon. Each of the four traces 162-168 disposed on the layer 160 is operably coupled to a specific separate one of the contacts 154A, 156A (not shown), 158A, 160A (not shown) and extends from the contact 154A-160A to the proximal end of the probe 150. Each trace 162-168 is electrically isolated from each other trace 162-168 disposed on the layer 160 and extends proximally toward a proximal end of the body 152 such that the proximal end of each trace 162-168 can be coupled to a proximal connector similar to any other embodiment of such a proximal connector disclosed or contemplated herein.

Each trace 162-168 has an elongate section 162A-168A that extends along the length of the layer 160 as discussed above. Further, each trace 162-168 also has a transverse (or "side") extension 162B-168B that extends from a distal end of the elongate section 162A-168A transversely in relation to the longitudinal axis of the elongate sections 162A-168A. More specifically, extension 162B extends toward side 152C of the layer 160 (and body 152), extension 168B extends toward side 152A, extension 164B extends toward either side 152B or 152D and extension 166B extends toward the other of sides 152B, 152D. Hence, each trace 162-168 is in contact with and electrically coupled to a different, separate contact of the four contacts 154A, 156A, 158A, 160A (not shown). In one embodiment, each extension 162B-168B is a separate electrical connection that is electrically coupled to the appropriate elongate section 162A-168A. Alternatively, each extension 162B-168B is an integral component of the appropriate elongate section 162A-168A such that each trace 162-168 is a single, unitary component with two sections.

It is understood that each of the other three layers (not shown) has a similar configuration, with four traces on each layer that are similar to the traces 162-168 on layer 160 except that they differ in the length of their elongate sections (as discussed below) and the four contacts to which they are connected. Further, it is understood that the device 150 can have any number of layers and any number of contacts in a similar fashion to other embodiments herein.

Figure 9A:
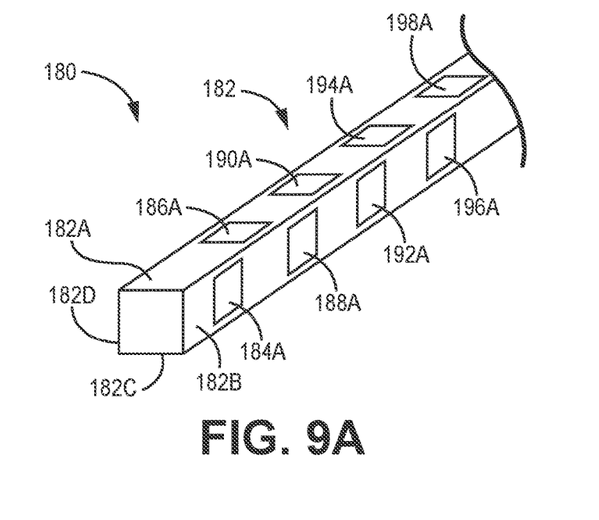
FIG. 9A is a perspective view of a distal portion of another depth electrode, according to another embodiment.
Figure 9B:
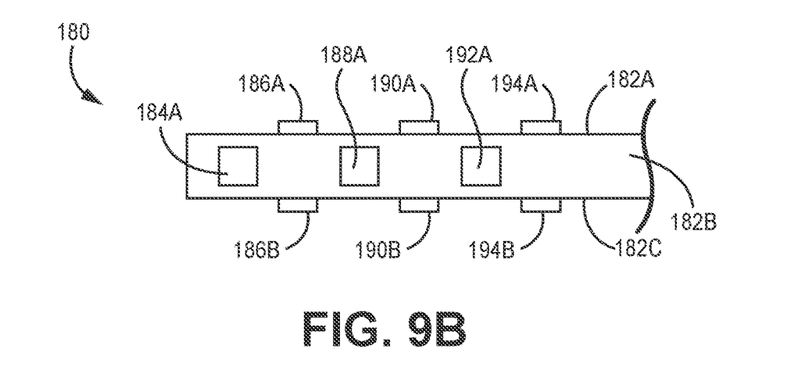
FIG. 9B is a side view of the distal portion of the depth electrode of FIG. 9A, according to one embodiment.
Figure 9C:
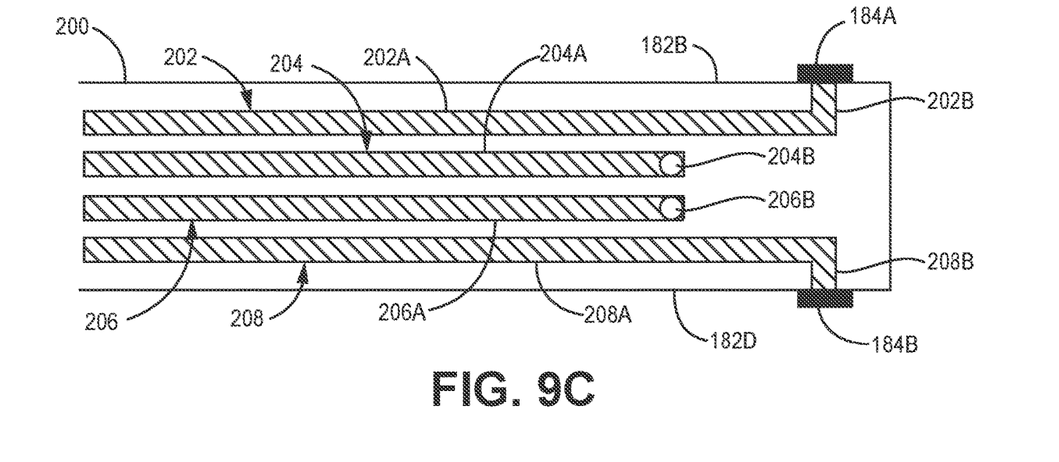
FIG. 9C is a top view of a distal portion of a layer of the depth electrode of FIG. 9A, according to one embodiment.

FIGS. 9A-9C depict a layered depth electrode 180 in accordance with one implementation that is composed of multiple thin film layers that are disposed in a stacked configuration to create a probe 180 having a relatively square or flat cross-section, according to one embodiment. As best shown in FIGS. 9A and 9B, the depth electrode 180 has a substantially square body 182. The body 182 can have dimensions substantially similar to those discussed above with respect to body 152. Alternatively, the body 182 can have any cross-sectional dimensions. The electrode 180 can have a length substantially similar to the electrode 150 discussed above.

Further, according to one embodiment, the body 182 has contacts 184A-198B, each of which is disposed on a side of the body 182. The contacts 184A-198B in this specific implementation are substantially square, but it is understood that the contacts 184A-198B can have any shape, including circular, quadrilateral, or any other known shape. Thus, the body 182 has a first side 182A with four contacts 186A, 190A, 194A, 198A disposed thereon, a second side 182B with four contacts 184A, 188A, 192A, 196A disposed thereon, a third side 182C with four contacts 186B, 190B, 194B, 196B (not shown) disposed thereon (as best shown in FIG. 9B), and a fourth side 182D (as best shown in FIG. 9A) with four contacts (not shown due to the perspective of the figures) disposed thereon. More specifically, there are eight sets of two contacts that are disposed at the same position along the length of the body 182 but on opposite sides of the body 182 thereof. Thus, the first set of two contacts 184A, 184B (not shown) is disposed near the distal end of the body 182, while the second set of two contacts 186A, 186B is disposed adjacent to the first set. Further, the third set of two contacts 188A, 188B (not shown) is disposed adjacent to the second set. the fourth set of two contacts 190A, 190B is disposed adjacent to the third set, the fifth set of two contacts 192A, 192B (not shown) is disposed adjacent to the fourth set, the sixth set of two contacts 194A, 194B is disposed adjacent to the fifth set, the seventh set of two contacts 196A, 196B (not shown) is disposed adjacent to the sixth set, and the eighth set of two contacts 198A, 198B (not shown) is disposed adjacent to the seventh set (and most distant from the distal end). Unlike certain other embodiments herein, none of the contacts on this electrode 180 encircle the body 182, and instead are disposed solely on one side of the body 182 as shown.

As mentioned above, the depth electrode 180 has a body 182 that has a layered (or "stacked") configuration in a fashion similar to the other device embodiments herein. That is, the body 182 is made up of layers of non-conductive thin film with traces disposed therebetween. For example, in one specific embodiment, the body 182 has four layers of non-conductive thin film (not shown) in a fashion similar to the device 10 depicted in FIG. 2A with four traces (not shown) disposed on each of the four layers (not shown). For example, as best shown in FIG. 9C, which depicts a top, cross-sectional view of one exemplary non-conductive thin film layer 200 (of the four layers of the body 182) with four traces 202, 204, 206, 208 disposed thereon. Each of the four traces 202-208 disposed on the layer 200 is operably coupled to a specific separate one of the contacts 184A, 184B (not shown), 186A, 186B and extends from the contact 184A-186B to the proximal end of the probe 180. Each trace 202-208 is electrically isolated from each other trace 202-208 disposed on the layer 200 and extends proximally toward a proximal end of the body 180 such that the proximal end of each trace 202-208 can be coupled to a proximal connector similar to any other embodiment of such a proximal connector disclosed or contemplated herein.

Each trace 202-208 has an elongate section 202A-208A that extends along the length of the layer 200 as discussed above. Further, each trace 202-208 also has a transverse (or "side") extension 202B-208B that extends from a distal end of the elongate section 202A-208A transversely in relation to the longitudinal axis of the elongate sections 202A-208A. More specifically, extension 202B extends toward side 182B of the layer 200 (and body 182), extension 208B extends toward side 182D, extension 204B extends toward either side 182A or 182C and extension 206B extends toward the other of sides 182A or 182C. Hence, each trace 202-208 is in contact with and electrically coupled to a different, separate contact of the four contacts 184A, 184B, 186A, 186B. In one embodiment, each extension 202B-208B is a separate electrical connection that is electrically coupled to the appropriate elongate section 202A-208A. Alternatively, each extension 202B-208B is an integral component of the appropriate elongate section 202A-208A such that each trace 202-208 is a single, unitary component with two sections.

It is understood that each of the other three layers (not shown) has a similar configuration, with four traces on each layer that are similar to the traces 202-208 on layer 200 except that they differ in the length of their elongate sections (as discussed below) and the four contacts to which they are connected. Further, it is understood that the device 180 can have any number of layers and any number of contacts in a similar fashion to other embodiments herein.

Figure 10A:
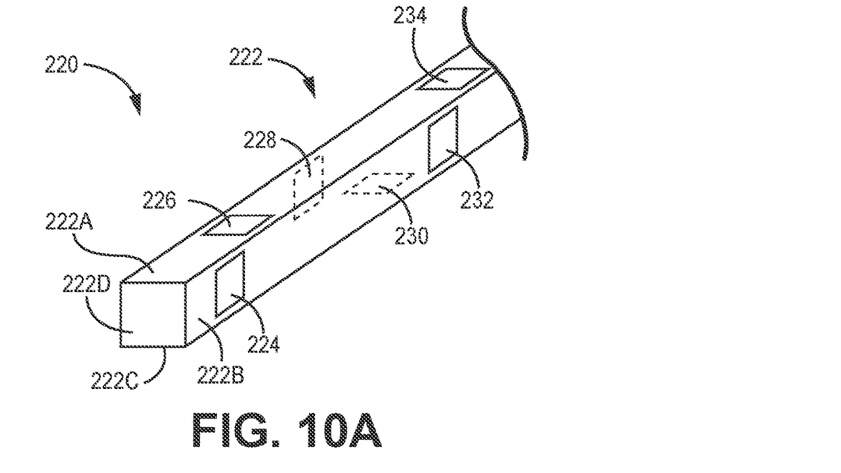
FIG. 10A is a perspective view of a distal portion of another depth electrode, according to another embodiment.
Figure 10B:
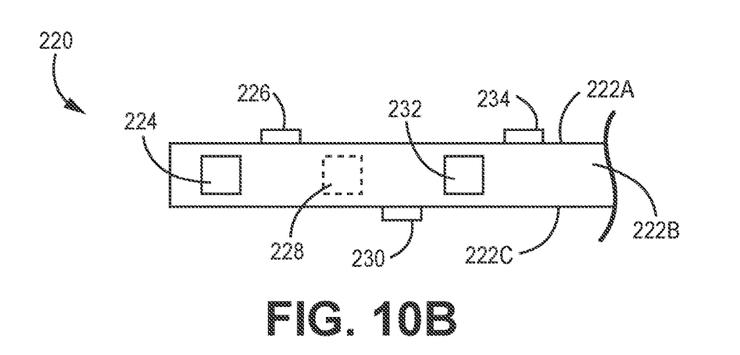
FIG. 10B is a side view of the distal portion of the depth electrode of FIG. 10A, according to one embodiment.
Figure 10C:
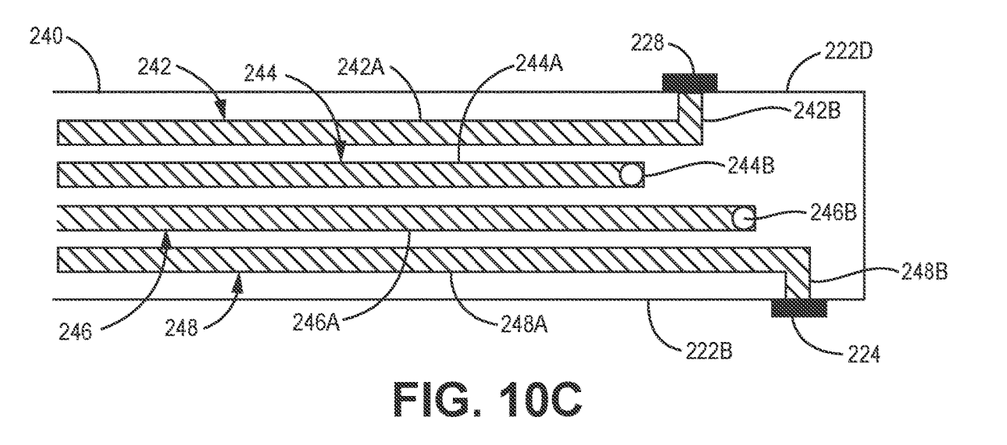
FIG. 10C is a top view of a distal portion of a layer of the depth electrode of FIG. 10A, according to one embodiment.

FIGS. 10A-10C depict a layered depth electrode 220 in accordance with one implementation that is composed of multiple thin film layers that are disposed in a stacked configuration to create a probe 220 having a relatively square or flat cross-section, according to one embodiment. As best shown in FIGS. 10A and 10B, the depth electrode 220 has a substantially square body 222. The body 222 can have dimensions substantially similar to those discussed above with respect to body 152. Alternatively, the body 222 can have any cross-sectional dimensions. The electrode 220 can have a length substantially similar to the electrode 150 discussed above.

Further, according to one embodiment, the body 222 has contacts 224-234, each of which is disposed on a side of the body 222. The contacts 224-234 in this specific implementation are substantially square, but it is understood that the contacts 224-234 can have any shape, including circular, quadrilateral, or any other known shape. Thus, the body 222 has a first side 222A with two contacts 226, 234 disposed thereon, a second side 222B with two contacts 224, 232 disposed thereon, a third side 222C with one contact 230 disposed thereon (as best shown in FIG. 10B), and a fourth side 222D (as best shown in FIG. 10A) with one contact 228 disposed thereon. More specifically, the contacts 224-234 are disposed on the sides 22A-222D in a spiral configuration along the length of the body 222 such that only one contact 224-234 is disposed at any one position with respect to the length of the body 222. Thus, the contact 224 is disposed on side 222B near the distal end of the body 222, while the second contact 226 is disposed adjacent to the first contact 224 and on the side 222A. Further, the third contact 228 is disposed adjacent to the second contact 226 and on the side 222D, while the fourth contact 230 is disposed adjacent to the third contact 228 and on the side 222C. In addition, the fifth contact 232 is disposed adjacent to the fourth contact 230 and on the side 222B, and the sixth contact 234 is disposed adjacent to the fifth contact 232 (and most distant from the distal end) and on the side 222A. It is understood that the device 220 can have additional contacts (not shown) disposed on the body 222 proximal to the sixth contact 234 that are simply not depicted in the figures. Further, it is understood that the device 220 can have any number of layers and any number of contacts. Unlike certain other embodiments herein, none of the contacts on this electrode 220 encircle the body 222, and instead each is disposed solely on one side of the body 222 as shown.

As mentioned above, the depth electrode 220 has a body 222 that has a layered (or "stacked") configuration in a fashion similar to the other device embodiments herein. That is, the body 222 is made up of layers of non-conductive thin film with traces disposed therebetween. For example, in one specific embodiment, the body 222 can have four layers of non-conductive thin film (not shown) in a fashion similar to the device 10 depicted in FIG. 2A with four traces (not shown) disposed on each of the four layers (not shown). For example, as best shown in FIG. 10C, which depicts a top, cross-sectional view of one exemplary non-conductive thin film layer 240 (of the layers of the body 222) with four traces 242, 244, 246, 248 disposed thereon. Each of the four traces 242-248 disposed on the layer 240 is operably coupled to a specific separate one of the contacts 224, 226, 228, 230 and extends from the contact 224-230 to the proximal end of the probe 220. Given that the device 220 has at least two additional contacts 232, 234, it is understood that at least one additional layer on which additional traces are coupled to those additional contacts. Each trace 242-248 is electrically isolated from each other trace 242-248 disposed on the layer 240 and extends proximally toward a proximal end of the body 220 such that the proximal end of each trace 242-248 can be coupled to a proximal connector similar to any other embodiment of such a proximal connector disclosed or contemplated herein.

Each trace 242-248 has an elongate section 242A-248A that extends along the length of the layer 240 as discussed above. Further, each trace 242-248 also has a transverse (or "side") extension 242B-248B that extends from a distal end of the elongate section 242A-248A transversely in relation to the longitudinal axis of the elongate sections 242A-248A. More specifically, extension 242B extends toward side 222D of the layer 240 (and body 222) and is coupled to contact 228, extension 248B extends toward side 222B and is coupled to contact 224, extension 244B extends toward either side 222A or 222C and extension 246B extends toward the other of sides 222A or 222C such that one of extensions 244B and 246B is coupled to contact 226 and the other is coupled to contact 230. Hence, each trace 242-248 is in contact with and electrically coupled to a different, separate contact of the four contacts 224-230. In one embodiment, each extension 242B-248B is a separate electrical connection that is electrically coupled to the appropriate elongate section 242A-248A. Alternatively, each extension 242B-248B is an integral component of the appropriate elongate section 242A-248A such that each trace 242-248 is a single, unitary component with two sections.

It is understood that each of the other layers (not shown) has a similar configuration, with as many as four traces or more on each layer that are similar to the traces 242-248 on layer 240 except that they differ in the length of their elongate sections (as discussed below) and the contacts to which they are connected. Further, it is understood that the device 220 can have any number of layers and any number of contacts in a similar fashion to other embodiments herein.

It is understood that any of the features, including the unique features, described with respect to any of the separate embodiments herein can be incorporated into any other implementations herein, so long as it doesn't impact the operability or functionality of the particular device.

Although the present invention has been described with reference to preferred embodiments, persons skilled in the art will recognize that changes may be made in form and detail without departing from the spirit and scope of the invention.

What is claimed is:

1. An intracranial electrode comprising an elongate body comprising:
    (a) a first elongate layer;
    (b) at least one first layer conductive connector disposed on and along a length of the first elongate layer, the at least one first layer conductive connector comprising a first side extension extending transversely from a distal end of the at least one first layer conductive connector toward one of an at least two elongate sides of the elongate body;
    (c) a second elongate layer attached to the first elongate layer such that the at least one first layer conductive connector is disposed between the first and second elongate layers, the second elongate layer comprising first and second partial layers;
    (d) a third elongate layer attached to the second elongate layer, wherein a lumen is defined by the first and second partial layers and the first and third elongate layers, wherein the lumen extends along a length of the elongate body;
    (e) at least one third layer conductive connector disposed on and along a length of the third elongate layer, the at least one third layer conductive connector comprising a third side extension extending transversely from a distal end of the at least one third layer conductive connector toward one of the at least two elongate sides of the elongate body;
    (f) at least one first layer contact coupled to the elongate body, wherein the at least one first layer contact is electrically coupled with the first side extension; and
    (g) at least one second layer contact coupled to the elongate body, wherein the at least one second layer contact is electrically coupled with the third side extension.

2. The intracranial electrode of claim 1, wherein the at least one first layer conductive connector is a thin-film conductive connector and the at least one third layer conductive connector is a thin-film conductive connector.

3. The intracranial electrode of claim 1, wherein the at least one first layer contact is disposed around the elongate body and the at least one second layer contact is disposed around the elongate body.

4. The intracranial electrode of claim 3, wherein the at least one first layer contact is disposed around a full outer circumference of the device body and the at least one second layer contact is disposed around the full outer circumference of the elongate body.

5. The intracranial electrode of claim 1, wherein the third elongate layer comprises at least one third layer opening defined in a proximal portion of the third elongate layer, wherein a proximal portion of the at least one third layer conductive connector is disposed through the at least one third layer opening and on and along a length of the first elongate layer.

6. The intracranial electrode of claim 1, further comprising:
   (a) a fourth elongate layer attached to the third elongate layer such that the at least one third layer conductive connector is disposed between the second and fourth elongate layers;
   (b) at least one fourth layer conductive connector disposed on and along a length of the fourth elongate layer, the at least one fourth layer conductive connector comprising a fourth side extension extending transversely from a distal end of the at least one fourth layer conductive connector one of the at least two elongate sides of the elongate body; and
   (c) at least one third layer contact coupled to the elongate body, wherein the at least one third layer contact is electrically coupled with the fourth side extension.

7. The intracranial electrode of claim 6, further comprising at least one second layer elongate conductive connector disposed on and along a length of the second elongate layer, the at least one second layer elongate conductive connector comprising a second side extension extending transversely from a distal end of the at least one second layer conductive connector toward one of the at least two elongate sides of the elongate body, wherein the second elongate layer comprises at least one second layer opening defined in a proximal portion of the second elongate layer, wherein a proximal portion of the at least one second layer elongate conductive connector is disposed through the at least one second layer opening and on and along a length of the first elongate layer.

8. The intracranial electrode of claim 6, further comprising:
   (a) a fifth elongate layer attached to the first elongate layer;
   (b) at least one fifth layer conductive connector disposed on and along a length of the fifth elongate layer such that the at least one fifth layer conductive connector is disposed between the first and fifth elongate layer, the at least one fifth layer conductive connector comprising a fifth side extension extending transversely from a distal end of the at least one fifth layer conductive connector toward one of the at least two elongate sides of the elongate body; and
   (c) at least one third layer contact coupled to the elongate body, wherein the at least one third layer contact is electrically coupled with the fifth side extension.

9. A depth electrode comprising an elongate body comprising:
   (a) a first elongate non-conductive layer;
   (b) at least one first layer elongate conductive connector disposed on and along a length of the first elongate non-conductive layer, the at least one first layer elongate conductive connector comprising a first side extension extending transversely from a distal end of the at least one first layer elongate conductive connector toward a side of the first elongate non-conductive layer;
   (c) a second elongate non-conductive layer attached to the first elongate non-conductive layer such that the at least one first layer elongate conductive connector is disposed between the first and second elongate non-conductive layers;
   (d) at least one second layer elongate conductive connector disposed on and along a length of the second elongate non-conductive layer, the at least one second layer elongate conductive connector comprising a second side extension extending transversely from a distal end of the at least one second layer elongate conductive connector toward a side of the second elongate non-conductive layer;
   (e) at least one first layer contact disposed around the elongate body, wherein the at least one first layer contact is electrically coupled with the first side extension; and
   (f) at least one second layer contact disposed around the elongate body, wherein the at least one second layer contact is electrically coupled with the second side extension; and
   (g) a third elongate non-conductive layer comprising first and second partial layers and a lumen defined by the first and second elongate non-conductive layers and the first and second partial layers, wherein the lumen extends along a length of the elongate body.

10. The depth electrode of claim 9, wherein the at least one first layer elongate conductive connector is a thin-film elongate conductive connector and the at least one second layer elongate conductive connector is a thin-film elongate conductive connector.

11. The depth electrode of claim 9, wherein the second elongate non-conductive layer comprises at least one second layer opening defined in a proximal portion of the second elongate non-conductive layer, wherein a proximal portion of the at least one second layer elongate conductive connector is disposed through the at least one second layer opening and on and along a length of the fourth elongate non-conductive layer.

12. The depth electrode of claim 9, further comprising:
   (a) a fourth elongate non-conductive layer attached to the second elongate non-conductive layer;
   (b) at least one fourth layer elongate conductive connector disposed on and along a length of the fourth elongate non-conductive layer, the at least one fourth layer elongate conductive connector comprising a fourth side extension extending transversely from a distal end of the at least one fourth layer elongate conductive connector toward a side of the fourth elongate non-conductive layer, wherein the at least one fourth layer elongate conductive connector is disposed between the second and fourth elongate non-conductive layers; and
   (c) at least one third layer contact disposed around the elongate body, wherein the at least one third layer contact is electrically coupled with the fourth side extension.

13. The depth electrode of claim 12, further comprising:
   (a) a fifth elongate non-conductive layer attached to the first elongate non-conductive layer such that the at least one first layer elongate conductive connector is disposed between the first and fifth elongate non-conductive layers;
   (b) at least one fifth layer elongate conductive connector disposed on and along a length of the fifth elongate non-conductive layer, the at least one fifth layer elongate conductive connector comprising a fifth side extension extending transversely from a distal end of the at least one fifth layer elongate conductive connector toward a side of the fifth elongate non-conductive layer; and
   (c) at least one fifth layer contact disposed around the elongate body, wherein the at least one fifth layer contact is electrically coupled with the fifth side extension.

14. The depth electrode of claim 9, wherein the lumen is constructed and arranged to allow for passage therethrough of a fluid, particulates, a procedural device, a stiffening device, a temperature probe, a steering mechanism, tissue, a treatment composition, or a medication.

15. A depth electrode comprising:
   (a) an elongate body comprising a stacked configuration of at least two non-conductive thin film layers,
   (b) a first elongate conductive thin film connector disposed on and along a length of a first layer of the at least two elongate non-conductive thin film layers, the first elongate conductive thin film connector comprising a first side extension extending transversely from a distal end of the first elongate conductive thin film connector toward a side of the elongate body;
   (c) a second elongate conductive thin film connector disposed on and along a length of a second layer of the at least two elongate non-conductive thin film layers, the second elongate conductive thin film connector comprising a second side extension extending transversely from a distal end of the second elongate conductive thin film connector toward the side of the elongate body;
   (d) a lumen defined within a first and second partial layers of a third layer of the at least two elongate non-conductive thin film layers and the first and second layers of the at least two elongate non-conductive thin film layers, wherein the lumen extends along a length of the elongate body;
   (e) a first contact attached to the elongate body, wherein the first contact is electrically coupled with the first side extension; and
   (f) a second contact attached to the elongate body, wherein the second contact is electrically coupled with the second side extension.

16. The depth electrode of claim 15, wherein the elongate body has a substantially rectangular or substantially square cross-sectional shape.

17. The depth electrode of claim 15, further comprising a liner disposed within the lumen.

* * * * *